(12) United States Patent
Su et al.

(10) Patent No.: US 11,389,342 B2
(45) Date of Patent: Jul. 19, 2022

(54) PULL-ON ABSORBENT ARTICLE WITH PAIR OF BELT SECTIONS

(71) Applicant: UNICHARM CORPORATION, Ehime (JP)

(72) Inventors: Beibei Su, Kagawa (JP); Shimpei Komatsu, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 861 days.

(21) Appl. No.: 16/313,156

(22) PCT Filed: May 11, 2017

(86) PCT No.: PCT/JP2017/017825
§ 371 (c)(1),
(2) Date: Dec. 26, 2018

(87) PCT Pub. No.: WO2018/003309
PCT Pub. Date: Jan. 4, 2018

(65) Prior Publication Data
US 2019/0151166 A1    May 23, 2019

(30) Foreign Application Priority Data
Jun. 27, 2016   (JP) .............................. JP2016-126913

(51) Int. Cl.
*A61F 13/494*      (2006.01)
*A61F 13/496*      (2006.01)
(Continued)

(52) U.S. Cl.
CPC ...... *A61F 13/494* (2013.01); *A61F 13/15585* (2013.01); *A61F 13/49* (2013.01);
(Continued)

(58) Field of Classification Search
CPC ............... A61F 13/15585; A61F 13/49; A61F 13/49011; A61F 13/49017; A61F 13/494;
(Continued)

(56) References Cited

U.S. PATENT DOCUMENTS

| 5,411,498 | A  | * | 5/1995 | Fahrenkrug | ............. | A61F 13/15 |
|           |    |   |        |            |               | 604/385.22 |
| 7,569,039 | B2 | * | 8/2009 | Matsuda    | ...........   | A61F 13/49011 |
|           |    |   |        |            |               | 604/385.29 |
| 9,333,121 | B2 | * | 5/2016 | Sakaguchi  | ............  | A61F 13/494 |

(Continued)

FOREIGN PATENT DOCUMENTS

| JP | H4-28365 A   | 1/1992 |
| JP | H8-507699 A  | 8/1996 |

(Continued)

OTHER PUBLICATIONS

International Search Report in PCT Application No. PCT/JP2017/017825, dated Jul. 18, 2017, 4pp.
(Continued)

*Primary Examiner* — Michele M Kidwell
(74) *Attorney, Agent, or Firm* — Hauptman Ham, LLP

(57) ABSTRACT

In a pull-on absorbent article, pairs of joining sections that join an absorbent main body and a pair of belt sections to each other are provided, one pair being disposed on a front side and the other pair being disposed on a rear side in a front-rear direction, the absorbent main body including an absorbent body and being provided in a vertical direction, the pair of belt sections expanding and contracting in a lateral direction; a portion between the pair of joining sections on the rear side does not expand and contract in the lateral direction; an expanding-contracting section is provided closer than the absorbent body to a non-skin side of a wearer; and, in at least the rear side, the expanding-con-
(Continued)

tracting section is provided at a central portion of the absorbent main body in the lateral direction.

8 Claims, 9 Drawing Sheets

(51) Int. Cl.
*A61F 13/49* (2006.01)
*A61F 13/15* (2006.01)

(52) U.S. Cl.
CPC ...... *A61F 13/496* (2013.01); *A61F 13/49011* (2013.01); *A61F 13/49473* (2013.01); *A61F 13/49017* (2013.01); *A61F 2013/15121* (2013.01)

(58) Field of Classification Search
CPC .............. A61F 13/49473; A61F 13/496; A61F 2013/15121
See application file for complete search history.

(56) References Cited

U.S. PATENT DOCUMENTS

| | | | |
|---|---|---|---|
| 2002/0010455 A1* | 1/2002 | Hermansson | A61F 13/49019 604/385.24 |
| 2003/0040732 A1* | 2/2003 | Ishikawa | A61F 13/496 604/385.29 |
| 2008/0097369 A1* | 4/2008 | Melander | A61F 13/5622 604/392 |
| 2009/0312739 A1* | 12/2009 | Umebayahi | A61F 13/15723 604/385.29 |
| 2012/0143162 A1* | 6/2012 | Mukai | A61F 13/49001 604/385.3 |
| 2012/0157953 A1* | 6/2012 | Ashton | A61F 13/49015 604/385.16 |
| 2013/0102982 A1* | 4/2013 | Nakano | A61F 13/49001 604/365 |
| 2019/0070042 A1* | 3/2019 | LaVon | A61F 13/15601 |

FOREIGN PATENT DOCUMENTS

| | | |
|---|---|---|
| JP | 2000-288017 A | 10/2000 |
| JP | 2004-236850 A | 8/2004 |
| JP | 2010-131197 A | 6/2010 |

OTHER PUBLICATIONS

Office Action in IN Application No. 201827045783, dated Jun. 13, 2021, 5pp.

\* cited by examiner

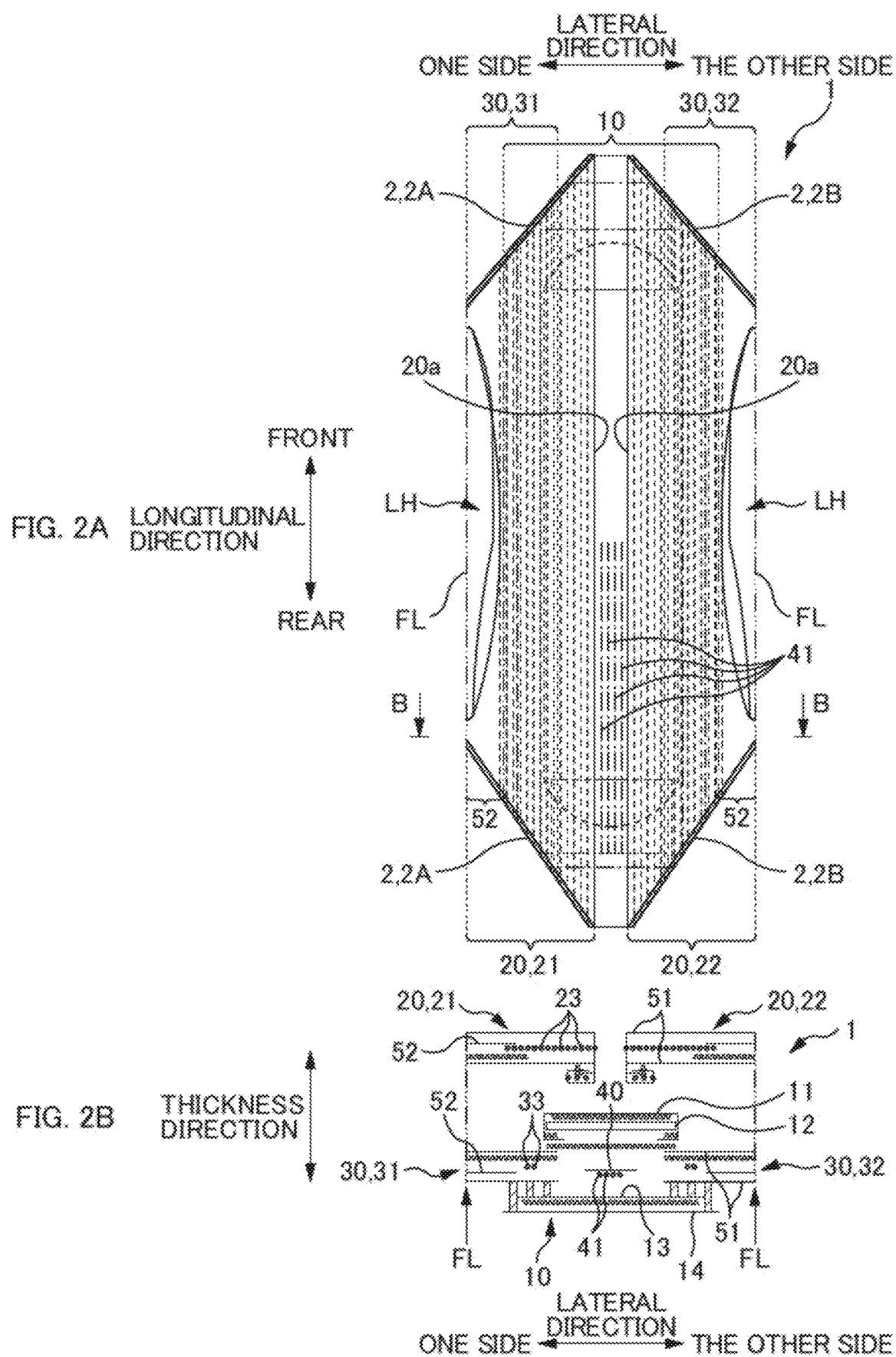

| | WAIST EXPANSION-CONTRACTION STRESS A(N) | BUTTOCKS EXPANSION-CONTRACTION STRESS B(N) | A/B | DISPLACEMENT AROUND WAIST | WEDGING INTO BUTTOCKS |
|---|---|---|---|---|---|
| EXAMPLE 1 | 5.56 | 0.37 | 15 | GOOD | GOOD |
| COMPARATIVE EXAMPLE 1 | 2.62 | 0.37 | 7.1 | TOLERABLE | GOOD |
| EXAMPLE 2 | 6.56 | 0.54 | 12.1 | GOOD | GOOD |
| COMPARATIVE EXAMPLE 2 | 6.56 | 0.98 | 6.7 | GOOD | TOLERABLE |

FIG. 8

PULL-ON ABSORBENT ARTICLE WITH PAIR OF BELT SECTIONS

RELATED APPLICATIONS

The present application is a national phase of International Application Number PCT/JP2017/017825, filed May 11, 2017, which claims priority to Japanese Application Number 2016-126913, filed Jun. 27, 2016.

TECHNICAL FIELD

The present invention relates to a pull-on absorbent article, and, particularly, to a sanitary pull-on absorbent article.

BACKGROUND ART

As a pull-on absorbent article, for example, Patent Literature 1 discloses a pull-on absorbent article that includes an absorbent main body having a liquid holding property and that is characterized in that edge portions on both sides of a front portion located at the front of a wearer and edge portions on both sides of a back portion located at the back of the wearer are joined to each other to form a waist opening and a pair of leg openings. In the pull-on absorbent article, in order to improve its fittability, an elastic member is disposed over the entire periphery of the waist opening, and a plurality of elastic members in a width direction are arranged at a buttocks abutting section and side by side in a longitudinal direction of the absorbent main body.

CITATION LIST

Patent Literature

PTL 1: Japanese Patent Application Publication No. 2000-288017

SUMMARY OF INVENTION

Technical Problem

Pull-on absorbent articles in which elastic members are arranged as described above do not look very much like underwear and have appearances that tend to be disliked. When such pull-on absorbent articles are used particularly as sanitary pull-on absorbent articles, since, for example, menstrual blood, which is a discharging substance, flows along the cleft between the buttocks and tends to leak, an absorbent body is required to closely fit the cleft between the buttocks. Therefore, pull-on absorbent articles, like those described above, whose elastic members are arranged over the entire buttocks abutting section and whose entire buttocks abutting section are made to fit a wearer, are inadequate in terms of preventing leakage; on the contrary, such pull-on absorbent articles are such that a tightening force is increased, thereby making the pull-on absorbent articles less comfortable to wear.

The present invention has been made in view of existing problems such as those described above, and an objective thereof is to provide a pull-on absorbent article, particularly, a sanitary pull-on absorbent article, that suppresses leakage of excrement while being underwear-like in appearance.

Solution to Problem

A main aspect of the present invention for accomplishing the above-described object is a pull-on absorbent article having a vertical direction, a lateral direction, and a front-rear direction and including a waist opening and a pair of leg openings, and comprises an absorbent main body that includes an absorbent body and that is provided in the vertical direction, and a pair of belt sections that are each disposed on a corresponding side of the absorbent main body in the lateral direction and that expand and contract in the lateral direction, wherein pairs of joining sections that join at least the absorbent main body and the pair of belt sections to each other are provided, one pair being disposed on a front side and the other pair being disposed on a rear side in the front-rear direction, at least a portion between the pair of joining sections on the rear side does not expand and contract in the lateral direction, an expanding-contracting section that expands and contracts in the vertical direction is provided closer than the absorbent body to a non-skin side of a wearer, and in at least the rear side, the expanding-contracting section is provided at a central portion of the absorbent main body in the lateral direction.

The other features of the present invention are made clearer by the present description and the attached drawings.

Advantageous Effects of Invention

According to the present invention, it is possible to provide a pull-on absorbent article, particularly, a sanitary pull-on absorbent article, that suppresses leakage of excrement while being underwear-like in appearance.

BRIEF DESCRIPTION OF DRAWINGS

FIG. 2A is a schematic view of the absorbent article 1 in a flat and expanded state, and FIG. 2B is a schematic sectional view along B-B in FIG. 2A.

FIG. 8 is a table of evaluated results obtained by measuring an expansion-contraction stress A and an expansion-contraction stress B in absorbent articles 1 of Examples 1 and 2 and Comparative Examples 1 and 2.

DESCRIPTION OF EMBODIMENTS

Figure 1:
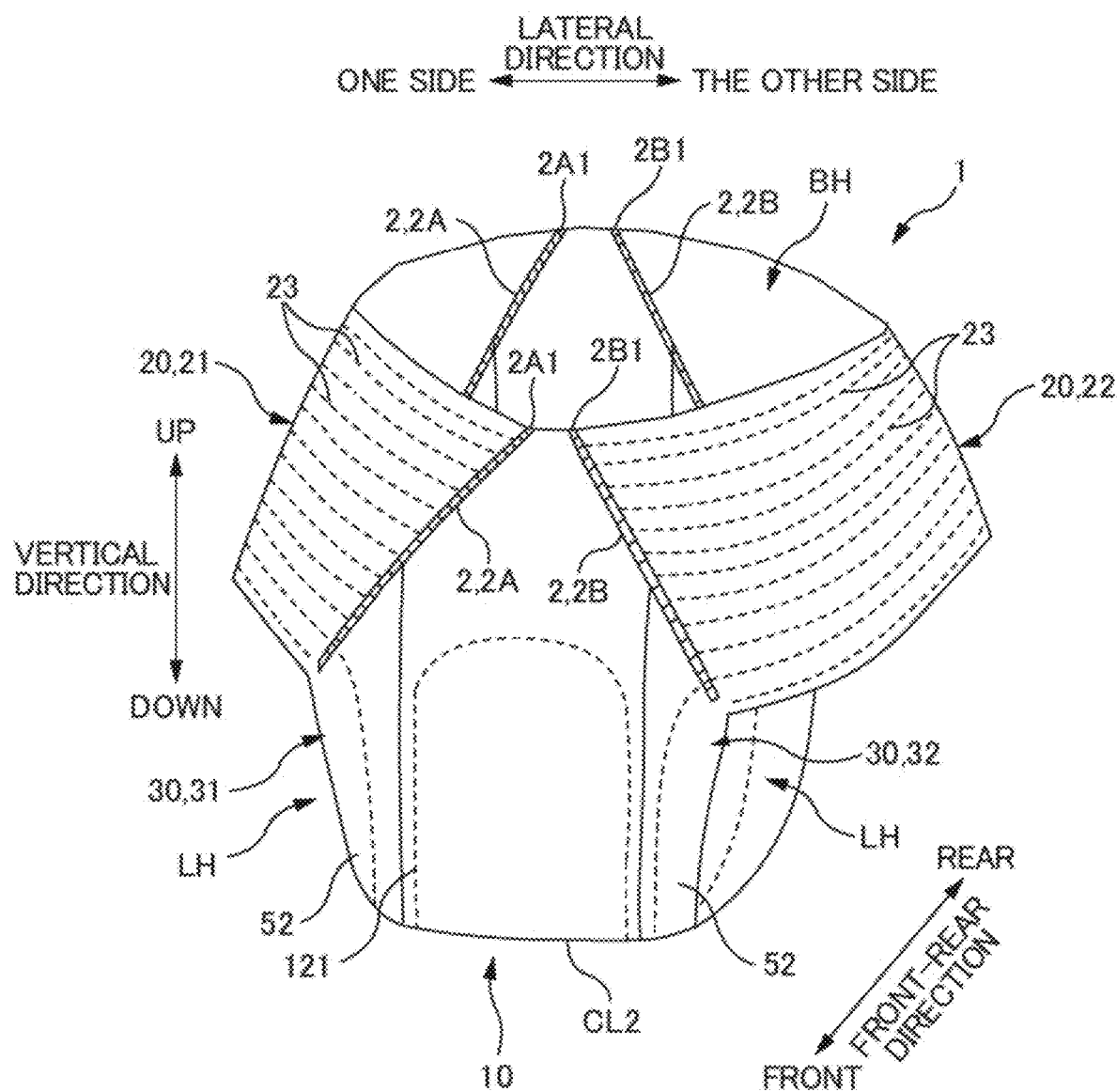
FIG. 1 is a schematic perspective view of a pull-on absorbent article 1.

The present description and the attached drawings make clear at least the following matters.

A pull-on absorbent article has a vertical direction, a lateral direction, and a front-rear direction and includes a waist opening and a pair of leg openings; and comprises an absorbent main body that includes an absorbent body and that is provided in the vertical direction, and a pair of belt sections that are each disposed on a corresponding side of the absorbent main body in the lateral direction and that expand and contract in the lateral direction, wherein pairs of joining sections that join at least the absorbent main body and the pair of belt sections to each other are provided, one pair being disposed on a front side and the other pair being disposed on a rear side in the front-rear direction, at least a portion between the pair of joining sections on the rear side does not expand and contract in the lateral direction, an expanding-contracting section that expands and contracts in the vertical direction is provided closer than the absorbent body to a non-skin side of a wearer, and in at least the rear side, the expanding-contracting section is provided at a central portion of the absorbent main body in the lateral direction.

According to such a pull-on absorbent article, even if, in order to provide an underwear-like appearance, a portion between the pair of joining sections on the rear side does not expand and contract in the lateral direction, since the expanding-contracting section causes the absorbent body to closely fit the cleft between the buttocks of a wearer, it is possible to suppress leakage of excrement.

In such a pull-on absorbent article, in the vertical direction, an upper end of the expanding-contracting section is positioned so as to match a position of an upper end of the absorbent body or is positioned on a lower side of the upper end of the absorbent body.

According to such a pull-on absorbent article, it is possible to prevent a region thereof situated above the absorbent body and having a low rigidity from becoming twisted (turned up at the wearer's back), and to firmly cover the upper portion of the buttocks of the wearer.

In such a pull-on absorbent article, in the vertical direction, a lower end of the expanding-contracting section is positioned so as to match a position of a lower end of the pull-on absorbent article or is positioned on the rear side and the upper side of the lower end of the pull-on absorbent article.

According to such a pull-on absorbent article, it is possible to cause the region of the absorbent body that corresponds to the buttocks and that is located on the rear side of the discharge opening of the wearer to closely fit the wearer and to suppress leakage of excrement.

Such a pull-on absorbent article comprises a waist section, wherein the waist section includes at least the pair of belt sections and an upper portion on the front side and an upper portion on the rear side of the absorbent main body in the vertical direction, and wherein an expansion-contraction stress of the waist section in the lateral direction when a length in the lateral direction of the waist section in a maximally expanded state in the lateral direction is reduced to 61% from the maximally expanded state is larger than an expansion-contraction stress of the expanding-contracting section in the vertical direction when a length in the vertical direction of the expanding-contracting section in a maximally expanded state in the vertical direction is reduced to 82% from the maximally expanded state.

According to such a pull-on absorbent article, it is possible to, while the expanding-contracting section causes the absorbent body to closely fit the cleft between the buttocks of the wearer, fit the waist section to the wearer and suppress displacement of the waist section that is worn.

Such a pull-on absorbent article comprises a pair of leg gather sections that are each disposed on a corresponding side of the absorbent main body in the lateral direction and that expand and contract in the vertical direction, wherein the expanding-contracting section and the leg gather sections have an overlapping section where the expanding-contracting section and each leg gather section overlap each other in the vertical direction, and wherein when the absorbent article has contracted from an expanded state to a natural state, a contraction amount in the vertical direction of the overlapping section at the expanding-contracting section is larger than a contraction amount in the vertical direction of the overlapping section at each leg gather section.

According to such a pull-on absorbent article, it is possible to prevent the leg gather sections from hindering the contraction of the expanding-contracting section in the vertical direction. Therefore, it is possible to, while causing the leg gather sections to closely fit the legs of the wearer, cause the expanding-contracting section to closely fit the absorbent body to the cleft between the buttocks of the wearer and suppress leakage of excrement from the waist and rearward leakage of excrement.

In the pull-on absorbent article, the expanding-contracting section is provided with a plurality of thread-like elastic members that are arranged side by side in the lateral direction, and each leg gather section is provided with a sheet-like elastic member at least along the leg opening corresponding thereto.

According to such a pull-on absorbent article, the contraction amount of the expanding-contracting section in the vertical direction is easily increased by the thread-like elastic members. Since each leg gather section closely fits the waist of the wearer at a surface, it is possible to reduce the burden on the skin.

In such a pull-on absorbent article, in the vertical direction, each joining section is tilted outward in the lateral direction toward the leg opening corresponding thereto from a side of the waist opening, and a perpendicular line that is perpendicular to the joining sections on the rear side crosses the expanding-contracting section.

According to such a pull-on absorbent article, it is possible to transfer a pulling-up force that the absorbent main body is subjected to from each belt section when the absorbent article is worn to the expanding-contracting section and to allow the expanding-contracting section to greatly expand in the vertical direction. Therefore, it is possible to, while the expanding-contracting section greatly contracts, cause the absorbent body to firmly and closely fit the cleft between the buttocks of the wearer.

In such a pull-on absorbent article, the perpendicular line is a perpendicular bisector of the joining sections on the rear side.

According to such a pull-on absorbent article, since the pulling-up force that the absorbent main body is subjected to from each belt section is increased on the perpendicular bisector of the joining sections, the expanding-contracting section is capable of greatly expanding in the vertical direction. Therefore, it is possible to, while the expanding-contracting section greatly contracts, cause the absorbent body to firmly and closely fit the cleft between the buttocks of the wearer.

In such a pull-on absorbent article, in the vertical direction, each joining section is tilted outward in the lateral direction toward the leg opening corresponding thereto from a side of the waist opening, and upper ends of the pair of joining sections on the rear side in the vertical direction are disposed apart from each other in the lateral direction, and the expanding-contracting section is positioned between positions of the upper ends in the lateral direction.

According to such a pull-on absorbent article, since the expanding-contracting section is less likely to be subjected to a pulling force in the lateral direction from each belt section, the expansion of the expanding-contracting section in the vertical direction is less likely to be hindered. Therefore, when pulling up the absorbent article, the expanding-contracting section is capable of greatly expanding in the vertical direction and the expanding-contracting section is capable of causing the absorbent body to firmly and closely fit the cleft between the buttocks of the wearer.

===Basic Configuration of Sanitary Pull-On Absorbent Article 1===

As a pull-on absorbent article of the present invention, a sanitary pull-on absorbent article 1 is taken as an example to describe an embodiment. However, the pull-on absorbent article of the present invention is not limited in its use to a sanitary pull-on absorbent article and is usable as, for example, a light incontinence diaper.

Figure 3A:
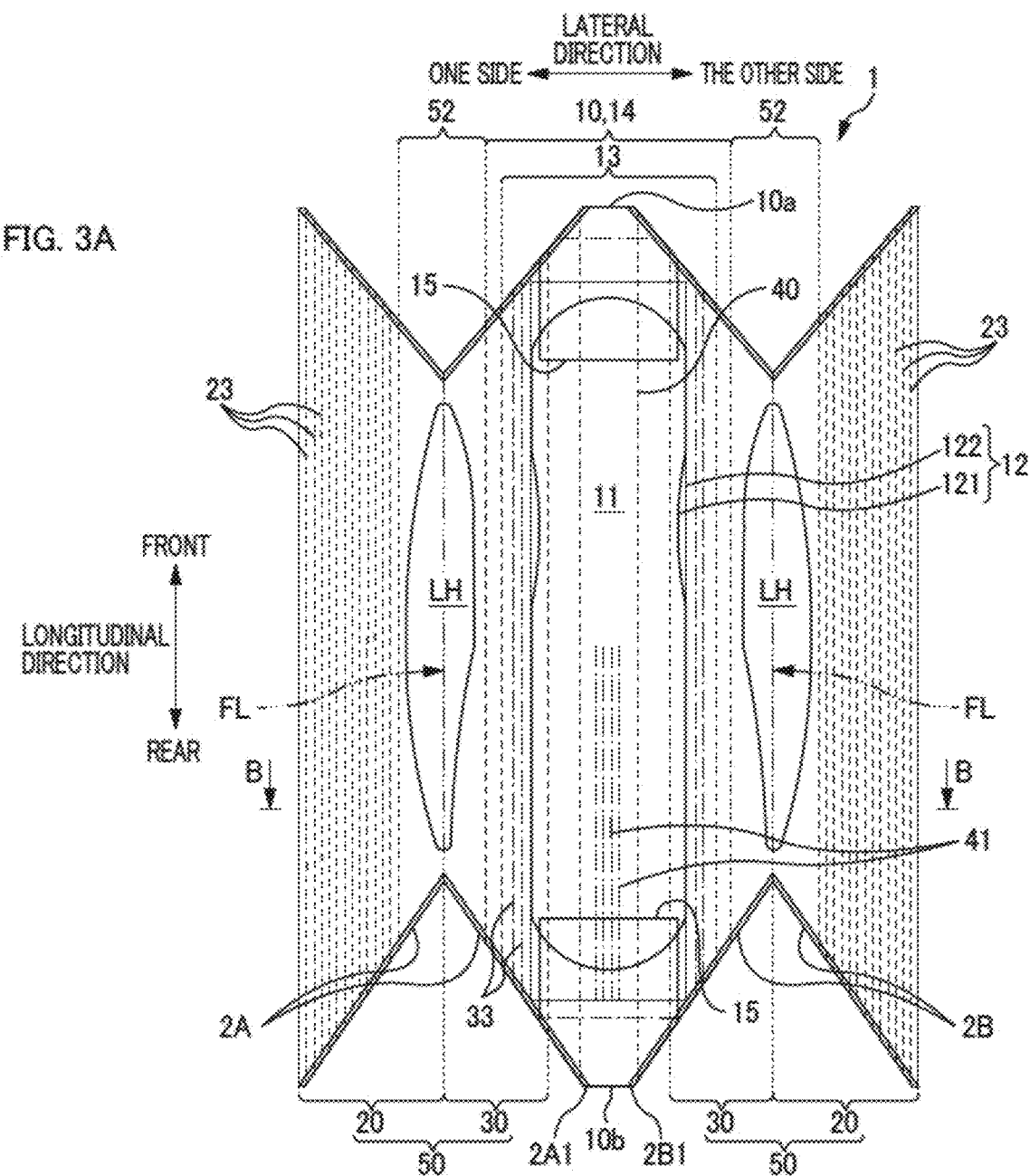
FIG. 3A is a schematic view in which joining sections 2 of the absorbent article 1 of FIG. 2A are disjoined from each other and belt sections 20 are opened outward in a lateral direction.
Figure 3B:
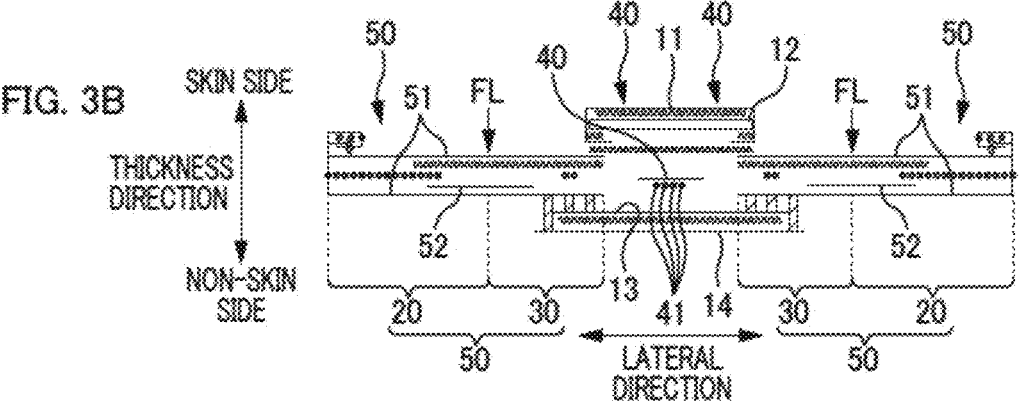
FIG. 3B is a schematic sectional view along B-B in FIG. 3A.

FIG. 1 is a schematic perspective view of the sanitary pull-on absorbent article 1 (absorbent article 1 below). FIG. 2A is a schematic view of the absorbent article 1 in a flat state and an expanded state, in which a longitudinal direction of an absorbent main body 10 and a longitudinal direction of each belt section 20 are the same. FIG. 2B is a schematic sectional view along B-B in FIG. 2A. FIG. 3A is a schematic view in which joining sections 2 of the absorbent article 1 in the flat state of FIG. 2A are disjoined from each other and the belt sections 20 are opened outward in a lateral direction. FIG. 3B is a schematic sectional view along B-B in FIG. 3A. Note that the wavy lines and hatched portions in FIGS. 2B and 3B indicate adhesives that join adjacent members together in a thickness direction and welding portions.

In a pull-on state shown in FIG. 1, the absorbent article 1 has a vertical direction, the lateral direction, and a front-rear direction that are orthogonal to one another. A waist opening BH and a pair of leg openings LH are formed in the absorbent article 1. In the vertical direction, the side of the waist opening BH is an upper side, and the side corresponding to the crotch of a wearer is a lower side. In the front-rear direction, the side corresponding to the front of the wearer is a front side, and the side corresponding to the back of the wearer is a rear side. The absorbent article 1 also has the thickness direction; and, in the thickness direction, the side that contacts the wearer is a skin side, and a side opposite thereto is a non-skin side.

In the pull-on state, the absorbent article 1 includes the absorbent main body 10 that is folded in two at a center CL2 in the longitudinal direction while, in the vertical direction, being provided in the longitudinal direction, the pair of belt sections 20 that are each disposed on a corresponding side of the absorbent main body 10 in the lateral direction and that expand and contract in the lateral direction, and a pair of leg gather sections 30 that are each disposed on a corresponding side of the absorbent main body 10 in the lateral direction in the longitudinal direction of the absorbent main body 10 and that expand and contract in the vertical direction. In the description below, of the pair of belt sections 20, the belt section on one side in the lateral direction is called a first belt section 21 and the belt section on the other side in the lateral direction is called a second belt section 22. Of the pair of leg gather sections 30, the leg gather section on one side in the lateral direction is called a first leg gather section 31 and the leg gather section on the other side in the lateral direction is called a second leg gather section 32.

The absorbent article 1 is provided with pairs of joining sections 2 that join the pair of belt sections 20 to the absorbent main body 10 and the pair of leg gather sections 30, one pair being disposed on the front side and the other pair being disposed on the rear side in the front-rear direction. In the vertical direction, each joining section 2 is tilted outward in the lateral direction toward the leg opening LH corresponding thereto from the waist opening side BH.

Specifically, in first joining sections 2A at the front and rear, inner end portions of the first belt section 21 in the lateral direction are joined to side portions of the absorbent main body 10 on an upper side in the vertical direction and on one side in the lateral direction and to an upper end portion of the first leg gather section 31 in the vertical direction. In second joining sections 2B at the front and rear, inner end portions of the second belt section 22 in the lateral direction are joined to side portions of the absorbent main body 10 on an upper side in the vertical direction and on the other side in the lateral direction and to an upper end portion of the second leg gather section 32 in the vertical direction.

Note that, examples of a method of forming the joining sections 2 may include welding processing, such as heat sealing and ultrasonic sealing, and bonding processing using an adhesive. In the description below, in each pair of joining sections 2, the joining section 2 on one side in the lateral direction is also called the first joining section 2A and the joining section 2 on the other side in the lateral direction is also called the second joining section 2B. It is desirable that the joining sections 2 be formed on a non-skin-side surface and so as not to reach the leg openings LH. This prevents the joining sections 2 that are harder than the other regions from coming into contact with the wearer and makes the absorbent article more comfortable to wear.

An upper end 2A1 of each first joining section 2A in the vertical direction and an upper end 2B1 of each second joining section 2B in the vertical direction are disposed apart from each other in the lateral direction. Therefore, in the absorbent article 1 in the pull-on state, the waist opening BH is formed by upper end portions of the pair of belt sections 20 in the vertical direction and vertical-direction upper end portions of the absorbent main body 10 at the front and rear. The leg openings LH are each formed by a lower end portion of the corresponding belt section 20 in the vertical direction and an outer side portion of the corresponding leg gather section 30 in the lateral direction. A region of each belt section 20 that becomes the waist opening BH is folded back a plurality of times as shown in FIG. 2B, so that the absorbent article has a durable structure that reduces the burden on the skin of the wearer.

The absorbent article 1 is brought into the flat state shown in FIG. 2A in the final stage of its manufacturing process. In the flat state, the longitudinal direction of the absorbent main body 10, the longitudinal direction of the pair of belt sections 20, and the longitudinal direction of the pair of leg gather sections 30 are the same. The pair of belt sections 20 are superimposed upon the absorbent main body 10 and the pair of leg gather sections 30 such that their skin side surfaces face one another. When, in the absorbent article 1 in the flat state, the absorbent main body 10 is folded in two at the center in the longitudinal direction while end portions 20a of the pair of respective belt sections 20 on the inner side in the lateral direction are pulled outward in the lateral direction, the absorbent article 1 is brought into the pull-on state of FIG. 1.

In the flat state, the absorbent article 1 is caused to expand in the longitudinal direction against the contraction force of each elastic member (for example, thread-like elastic members 23 of the belt sections 20 described below) arranged in the absorbent article 1, and the absorbent article 1 is caused to expand at portions thereof where the elastic members are arranged until wrinkles and the gathers can substantially no longer be seen.

<Absorbent Main Body 10>

In the absorbent main body 10, a top sheet 11, an absorbent body 12, a back sheet 13, an elastic member covering sheet 40, four buttocks elastic members 41, and an exterior sheet 14 are laminated to each other in this order from the skin side in the thickness direction. A pair of end-portion sheets 15 are each provided on a corresponding end portion of the absorbent main body 10 in the longitudinal direction (corresponding upper end portion in the vertical direction in the pull-on state) and closer to the skin side than the absorbent body 12 in the thickness direction.

The top sheet 11 is a liquid-permeable sheet, and an example thereof may be an air-through nonwoven fabric and the like. The back sheet 13 is a liquid-impermeable sheet, and an example thereof may be a polyethylene film or a polypropylene film and the like. The top sheet 11 and the back sheet 13 have sizes that allow the entire absorbent body 12 to be covered. Both side portions of the top sheet 11 of the present embodiment in the lateral direction are folded toward the non-skin-side surface side of the absorbent body 12. The exterior sheet 14 and the end-portion sheets 15 may be a liquid-permeable sheet or a liquid-impermeable sheet, and are desirably a soft sheet, such as a nonwoven fabric.

The absorbent body 12 is provided with an absorbent core 121 that absorbs a liquid and with a core-wrapping sheet 122 that covers an outer peripheral surface of the absorbent core 121. The absorbent core 121 is made of a liquid-absorbent material molded into a predetermined shape, and, in the present embodiment, has a substantially rectangular shape in which both ends of the absorbent core 121 in the longitudinal direction are curved. Examples of the liquid-absorbent material may include a material containing, for example, a superabsorbent polymer (so-called SAP) in a liquid-absorbent fiber, such as pulp fiber. Examples of the core-wrapping sheet 122 may include liquid-permeable sheets, such as tissue paper and a nonwoven fabric. Note that the core-wrapping sheet 122 need not be provided.

As shown in FIG. 3A, the elastic member covering sheet 40 is provided at a central portion of the absorbent main body 10 in the lateral direction from a longitudinal-direction front end 10a to a longitudinal-direction rear end 10b of the absorbent main body 10 in the longitudinal direction. The length of the elastic member covering sheet 40 in the lateral direction is relatively short, and is about the same as the length between the upper end 2A1 of the first joining section 2A and the upper end 2B1 of the second joining section 2B. The elastic member covering sheet 40 is a nonflexible sheet and an example thereof may be a nonwoven fabric and the like as with the exterior sheet 14.

The four buttocks elastic members 41 are provided at a region of the elastic member covering sheet 40 on the rear side in the longitudinal direction. The four buttocks elastic members 41 are arranged side by side and apart from one another with gaps therebetween in the lateral direction, and, in an expanded state in the longitudinal direction, are fixed to the elastic member covering sheet 40. Therefore, in the pull-on absorbent article 1 in a natural state, the four buttocks elastic members 41 are expandable and contractable in the vertical direction (are expandable and contractable in the longitudinal direction of the absorbent main body 10). Of each buttocks elastic member 41, only a region thereof that exhibits flexibility (a so-called effective length region) is illustrated. Therefore, regions of the elastic members that do not exhibit flexibility may exist on outer sides of the illustrated buttocks elastic members 41 in the longitudinal direction. A region of the absorbent main body 10 where each of the four buttocks elastic members 41 that exhibits flexibility are provided (a region 42 that is described later and that is surrounded by thick lines in FIG. 4) corresponds to an expanding-contracting section of the present invention, and may be called "buttocks expanding-contracting section 42" in the description below.

Note that the number of buttocks elastic members 41 is not limited to four. The buttocks expanding-contracting section 42 need not be formed from a thread-like elastic member. For example, as the buttocks expanding-contracting section 42, a plurality of sheet-like elastic members, such as flexible films or flexible nonwoven fabrics, or strips of elastic strings may be arranged apart from each other with intervals therebetween in the lateral direction; one sheet-like elastic member having the same size as the buttocks expanding-contracting section 42 may be disposed; or a thread-like elastic member and a sheet-like elastic member may both be disposed.

<Belt Sections 20 and Leg Gather Sections 30>

In the absorbent article 1 in the pull-on state, the belt sections 20 expand and contract in the lateral direction, and the leg gather sections 30 expand and contract in the vertical direction. Therefore, the absorbent article 1 fits around the waist and around the legs of the wearer. Therefore, in each belt section 20, the plurality of thread-like elastic members 23 in the longitudinal direction (substantially lateral direction) of the corresponding belt section 20 are arranged side by side in a width direction (a substantially vertical direction) of the corresponding belt section 20. In each leg gather section 30, a plurality of thread-like elastic members 33 (here, two thread-like elastic members 33) in the vertical direction are arranged side by side in the lateral direction. Sheet-like elastic members 52 are arranged at regions along the leg openings LH at the leg gather sections 30 and at the belt sections 20.

Note that an example of each of the thread-like elastic members 23 and 33 may be an elastic string and the like. An example of each sheet-like elastic member 52 may be a nonwoven fabric that is made to exhibit flexibility by performing a so-called gear stretching operation on a nonwoven fabric containing a substantially elastic elastomer fiber, such as a polyurethane-based elastomer, and a substantially non-elastic thermoplastic resin fiber, such as a polyolefin-based resin.

In the present embodiment, as shown in FIG. 3, the belt sections 20 and the leg gather sections 30 are formed from similar sheet members 50. In each sheet member 50, the thread-like elastic members 23 of the belt sections 20 and the thread-like elastic members 33 of the leg gather sections 30, as well as the sheet-like elastic members 52 are fixed in an expanded state between two sheets 51. It is desirable that the two sheets 51 be soft sheets, such as nonwoven fabrics. The holes (LH) for the leg openings are formed in regions of the sheet members 50 where the sheet-like elastic members 52 exist.

In the process of manufacturing the absorbent article 1, a pair of the sheet members 50 are disposed, one on each side of the absorbent main body 10 in the lateral direction. Specifically, an end portion of each sheet member 50 on the inner side in the lateral direction is inserted between the absorbent body 12 and the back sheet 13 to join them to each other. Then, at each folding-back line FL that is provided in the longitudinal direction of the corresponding sheet member 50 and that extends through the corresponding leg opening hole (LH), each sheet member 50 is folded back toward the skin-side surface side of the absorbent main body 10. With the folding line FL of each sheet member 50 being a boundary, a region that is superimposed upon the absorbent main body 10 in the thickness direction becomes the corresponding belt section 20, and a region that is arranged side by side in the lateral direction with the absorbent main body 10 becomes the corresponding leg gather section 30. By forming the pair of joining sections 2, the folded-back state of each sheet member 50 is fixed, and the absorbent article 1 in the flat state shown in FIG. 2 is formed. Note that the belt sections 20 and the leg gather sections 30 may be formed from different members.

===Buttocks Expanding-Contracting Section 42===

Figure 4:
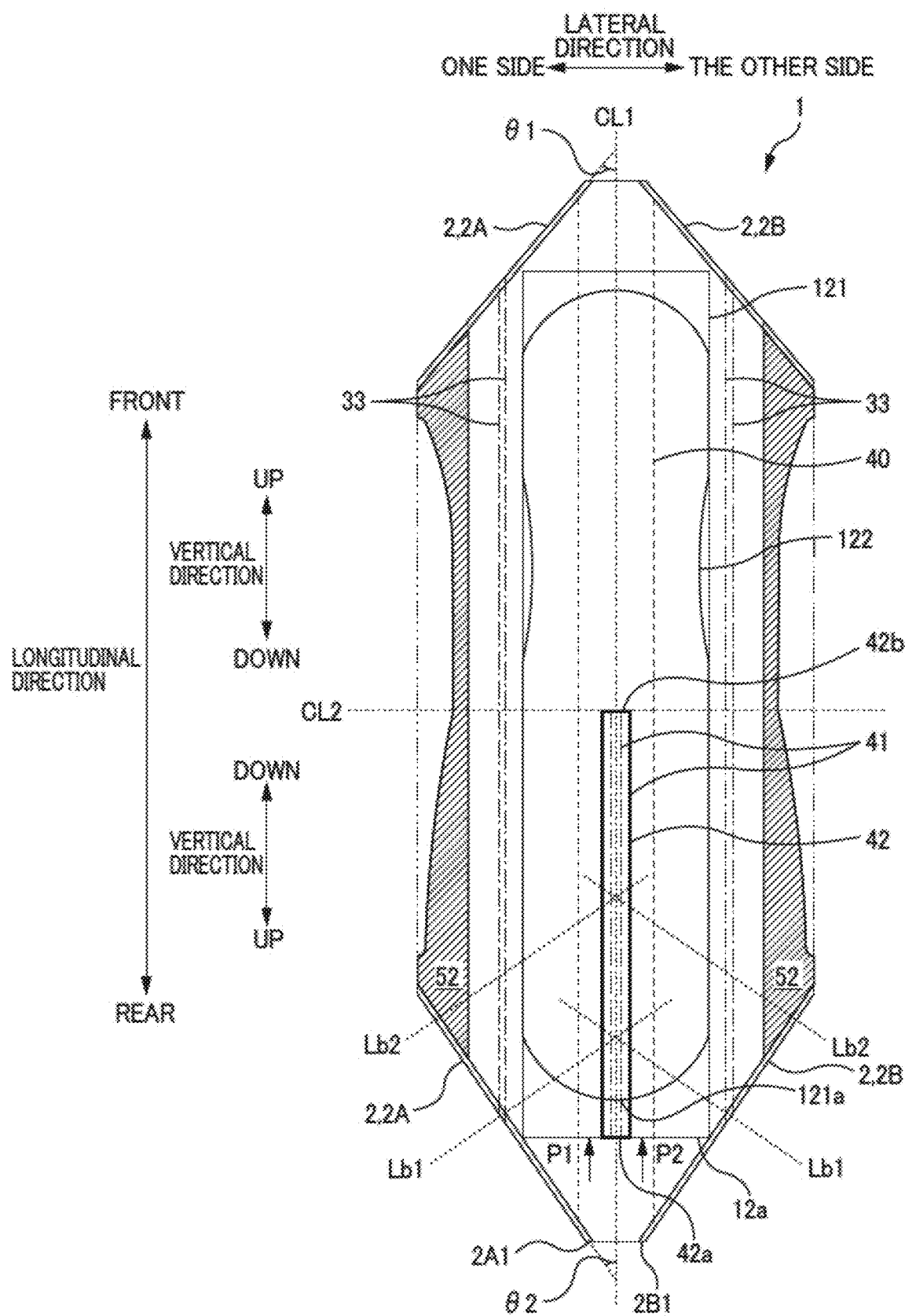
FIG. 4 is a schematic plan view of the absorbent article 1 in the flat and expanded state.
Figure 5:
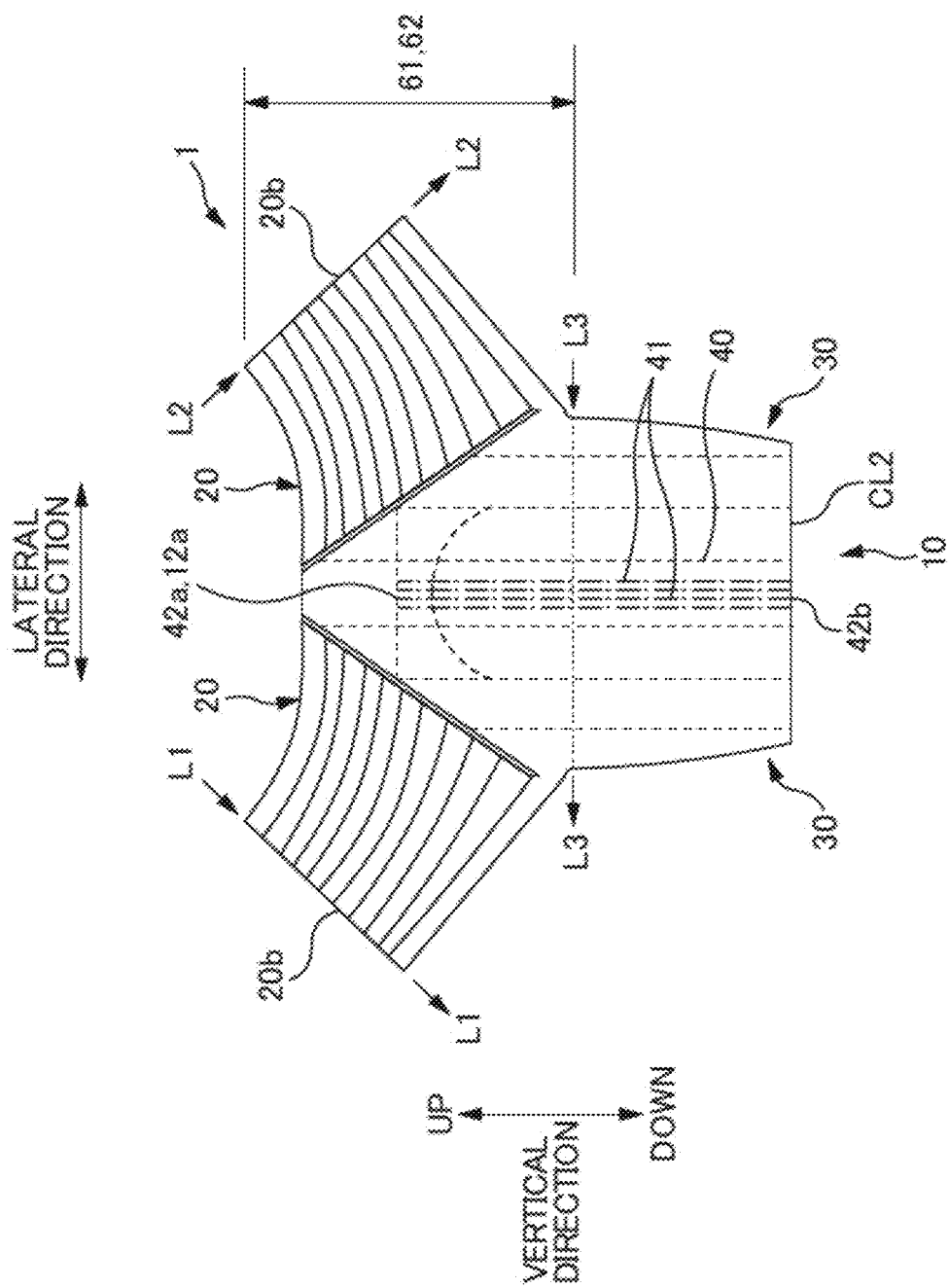
FIG. 5 is a rear view of the absorbent article 1 in a pull-on state.
Figure 6:
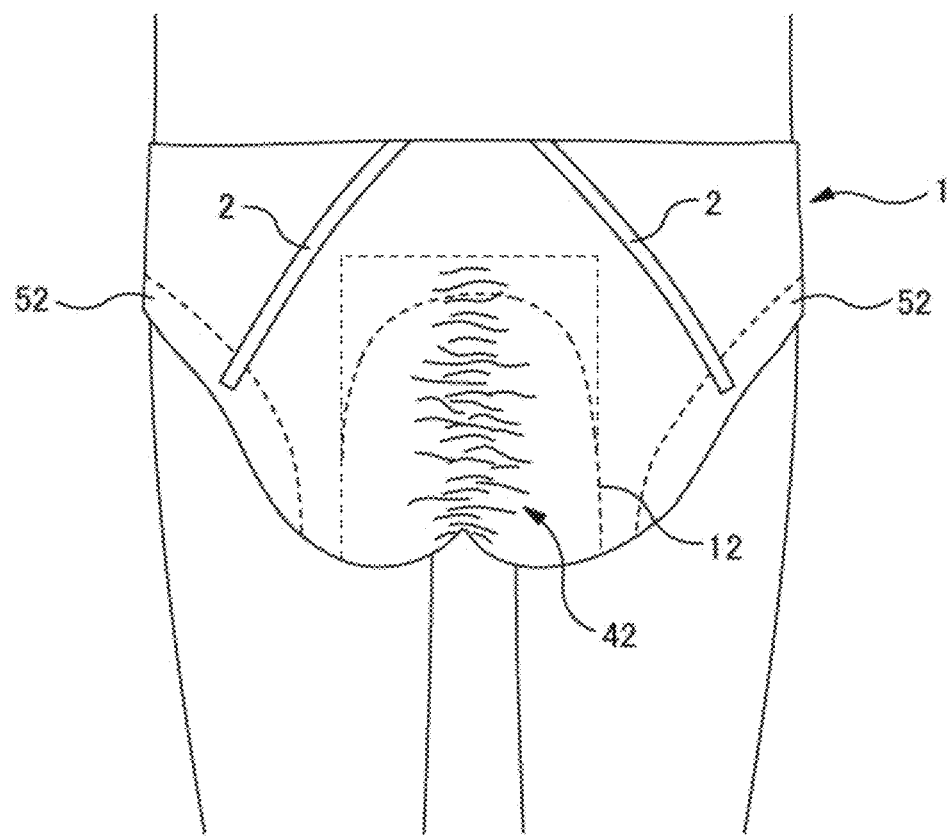
FIG. 6 is a rear view of the absorbent article 1 that is worn.

FIG. 4 is a schematic plan view of the absorbent article 1 in the flat state and the expanded state. FIG. 5 is a rear view of the absorbent article 1 in the pull-on state. FIG. 6 is a rear view of the absorbent article 1 that is worn.

Since, as with the absorbent article 1 of the present embodiment, a sanitary pull-on absorbent article is used by women, the absorbent article needs to be particularly underwear-like in appearance. As described above, in the absorbent article 1, elastic members in the lateral direction are not arranged between the pair of joining sections 2 and the portion between the pair of joining sections 2 does not expand and contract in the lateral direction. Therefore, compared to, for example, an absorbent article in which thread-like elastic members are arranged around the entire periphery of the waist, the absorbent article 1 is underwear-like in appearance. Further, in the vertical direction, the joining sections 2 forming the pair each extend toward the corresponding leg-opening-section-LH side from the waist-opening-section-BH side and are tilted outward in the lateral direction. Therefore, compared to, for example, an absorbent article in which the joining sections are provided in the vertical direction, the absorbent article 1 is underwear-like in appearance.

By not allowing the portion between the pair of joining sections 2 to expand and contract in the lateral direction, the expansion-contraction region becomes smaller, and a tight feeling is suppressed. In addition, the movement of the buttocks and the movement of the legs toward the front and the rear of the absorbent article 1 when, for example, the wearer is walking are not hindered by the elastic members. Therefore, the absorbent article 1 becomes more comfortable to wear.

On the other hand, if elastic members are not disposed at the portion between the pair of joining sections 2 and the portion between the pair of joining sections 2 does not expand and contract in the lateral direction, the absorbent main body 10 between the pair of joining sections 2 is less likely to fit the wearer closely, as a result of which a gap may be formed between the absorbent main body 10 and the wearer. This causes excrement to leak out easily.

When the pull-on absorbent article is used as a diaper, it is desirable that the rear portion of the absorbent article have the shape of a cup to provide a space that accommodates feces. On the other hand, when the pull-on absorbent article is used as a sanitary pull-on absorbent article, it is not necessary to accommodate feces. In addition, for example, menstrual blood, which is excrement, in sanitary items has higher viscosity than urine and flows along the cleft between the buttocks after being discharged from the vaginal opening, and tends to leak rearward. As a case in which a pull-on absorbent article is used instead of sanitary napkins, there may be a case in which the wearer is asleep and cannot change the pull-on absorbent article for a long time. Therefore, improvements need to be made, particularly, in terms of rearward leakage of excrement in sanitary pull-on absorbent articles.

Therefore, in the absorbent article 1 of the present embodiment, on the rear side (back side), the buttocks expanding-contracting section 42 (four buttocks elastic members 41) that expands and contracts in the vertical direction is provided at a central portion of the absorbent main body 10 in the lateral direction. As shown in FIG. 2B, the buttocks expanding-contracting section 42 is provided closer than the absorbent body 12 to the non-skin side of the wearer (non-skin side in the thickness direction).

Therefore, as shown in FIG. 6, in the absorbent article 1 that is worn, a region of the absorbent body 12 where the buttocks expanding-contracting section 42 is provided fits closely to the cleft between the buttocks of the wearer. Specifically, after the wearer has inserted their legs into the pair of leg openings LH when wearing the absorbent article 1, the pair of belt sections 20 are pulled obliquely upward. This causes the absorbent main body 10 to be pulled upward, and the buttocks expanding-contracting section 42 expands in the vertical direction. Thereafter, when the absorbent main body 10 has been pulled up to the crotch of the wearer to adjust the position of the absorbent article 1 with respect to the wearer, the buttocks expanding-contracting section 42 contracts, and the region of the absorbent body 12 where the buttocks expanding-contracting section 42 is provided closely fits the cleft between the buttocks of the wearer. Therefore, for example, menstrual blood that flows along the cleft between the buttocks from the discharge opening can be properly absorbed by the absorbent body 12. Therefore, even if the portion between the pair of joining sections 2 on the rear side do not expand and contract in the lateral direction, it is possible to suppress rearward leakage of excrement. In this way, the absorbent article 1 is capable of suppressing leakage of excrement while being underwear-like in appearance. Note that a portion between the pair of joining sections 2 on the front side may expand and contract in the lateral direction.

As shown in FIGS. 4 and 5, an upper end 42a (end on the rear side in the longitudinal direction)) of the buttocks expanding-contracting section 42 in the vertical direction is positioned so as to match the position of an upper end 12a (end on the rear side in the longitudinal direction) of the absorbent body 12. In this way, in the vertical direction of the absorbent article 1 in the pull-on state, it is desirable that the upper end 42a of the buttocks expanding-contracting section 42 be positioned so as to match the position of the upper end 12a of the absorbent body 12 or be positioned on the lower side of the upper end 12a of the absorbent body 12.

A region that is situated above the absorbent body 12 and that is formed from, for example, the exterior sheet 14 has a rigidity that is lower by an amount corresponding to the non-existence of the absorbent body 12. Therefore, if the buttocks expanding-contracting section 42 is positioned on the upper side of the absorbent body 12, the region that is situated above the absorbent body 12 becomes twisted (turned up at the wearer's back) by the buttocks expanding-contracting section 42. Therefore, by providing the buttocks expanding-contracting section 42 at a region where the absorbent body 12 exists and that has a high rigidity, it is possible to prevent the region above the absorbent body 12 from becoming twisted. As a result, the upper portion of the buttocks of the wearer can be properly covered. In addition, it is possible to prevent a deterioration in the appearance and a reduction in wearing comfort. However, the position is not limited to the above, such that the buttocks expanding-contracting section 42 may be positioned on the upper side of the upper end 12a of the absorbent body 12.

Of the absorbent body 12, a region thereof where the absorbent core 121 exists has a high rigidity. Therefore, although not illustrated, it is more desirable that the upper end 42a of the buttocks expanding-contracting section 42 be positioned so as to match the position of an upper end 121a of the absorbent core 121, or be positioned on the lower side of the upper end 121a of the absorbent core 121. This makes it possible to more reliably prevent the absorbent main body 10 from becoming twisted by the buttocks expanding-contracting section 42.

On the other hand, as shown in FIGS. 4 and 5, a lower end 42b (end on the front side in the longitudinal direction) of the buttocks expanding-contracting section 42 in the vertical direction is positioned so as to match the position of a lower end CL2 of the absorbent article 1 in the pull-on state. In this way, in the vertical direction of the absorbent article 1 in the pull-on state, it is desirable that the lower end 42b of the buttocks expanding-contracting section 42 be positioned so as to match the position of the lower end CL2 of the absorbent article 1, or be positioned on the rear side and the upper side of the lower end CL2 thereof. In the absorbent article 1 in the pull-on state, the absorbent main body 10 is folded in two at the center CL2 in the longitudinal direction. Therefore, in other words, it is desirable that the end 42b of the buttocks expanding-contracting section 42 on the front side in the longitudinal direction be positioned so as to match the position of the center CL2 of the absorbent main body 10 in the longitudinal direction, or be positioned on the longitudinal-direction rear side of the center CL2 thereof. This allows a region of the absorbent body 12 corresponding to the buttocks on the rear side of the discharge opening of the wearer to closely fit the wearer, and leakage of excrement to be suppressed.

The position is not limited to the above, such that the buttocks expanding-contracting section 42 may extend up to a portion on the front side of the longitudinal-direction center CL2 of the absorbent main body 10. Even in this case, the buttocks expanding-contracting section 42 is capable of causing a region of the absorbent body 12 corresponding to the discharge opening of the wearer to closely fit the wearer. However, at the region of the absorbent body 12 corresponding to the discharge opening of the wearer, in general, the basis weight of the absorbent core 121 is high, and the effect of close fittability realized by the buttocks expanding-contracting section 42 is less likely to be produced. Therefore, by providing the buttocks expanding-contracting section 42 in a region that produces high effects as described above and making the buttocks expanding-contracting section 42 as short as possible, it is possible to aim at reducing costs.

When the joining sections 2 are tilted with respect to the vertical direction, an underwear-like appearance is realized; however, the joining sections 2 may extend in the vertical direction.

In the case where the joining sections 2 are tilted, when the absorbent article 1 is pulled up and worn, the absorbent main body 10 is subjected to a pulling force in a direction orthogonal to the joining sections 2 from the belt sections 20 via the joining sections 2. Therefore, as shown in FIG. 4, it is desirable that perpendicular lines Lb1 and Lb2 perpendicular to the joining sections 2 on the rear side cross the buttocks expanding-contracting section 42. Note that the perpendicular lines perpendicular to the joining sections 2 may be perpendicular lines that are drawn from the position of either one of the joining sections 2. Accordingly, when the absorbent article 1 is pulled up, the pulling force from the belt sections 20 is transferred to the buttocks expanding-contracting section 42, and the buttocks expanding-contracting section 42 can be greatly expanded in the vertical direction. When the wearer positions the absorbent article 1, the buttocks expanding-contracting section 42 is capable of causing the absorbent body 12 to firmly and closely fit the cleft between the buttocks of the wearer while the buttocks expanding-contracting section 42 greatly contracts by an amount corresponding to the large expansion of the buttocks expanding-contracting section 42.

When the absorbent article 1 is pulled up, the pulling force from the belt sections 20 becomes stronger on the perpendicular bisectors Lb1 of the joining sections 2. Therefore, it is more desirable that the perpendicular bisectors Lb1 of the joining sections 2 on the rear side cross the buttocks expanding-contracting section 42. This makes it possible to, when pulling up the absorbent article 1, more greatly expand the buttocks expanding-contracting section 42, and to, thereafter, firmly and closely fit the absorbent body 12 to the cleft between the buttocks of the wearer while the buttocks expanding-contracting section 42 contracts more greatly.

After the absorbent article 1 has been pulled up by a certain extent, the wearer often further pulls up the absorbent article 1 by putting their hands therein from the lower end sides of the belt sections 20 to cause the absorbent main body 10 to fit the crotch of the wearer. At this time, the pulling force from each belt section 20 becomes stronger on the perpendicular lines Lb2 with respect to the lower end portions of the joining sections 2. Therefore, it is more desirable that the perpendicular lines Lb2 with respect to the lower end portions of the joining sections 2 on the rear side cross the buttocks expanding-contracting section 42. This makes it possible to, when pulling up the absorbent article 1, more greatly expand the buttocks expanding-contracting section 42, and to, thereafter, firmly and closely fit the absorbent body 12 to the cleft between the buttocks of the wearer while the buttocks expanding-contracting section 42 contracts more greatly.

The width (lateral-direction length) of the buttocks expanding-contracting section 42 should not be too large, and is, desirably, a width that allows the absorbent body 12 to closely fit the cleft between the buttocks of the wearer. Specifically, the width is desirably less than or equal to 25 mm and is on the order of 15 mm. In the absorbent article 1, as shown in FIG. 4, although the vertical-direction upper end 2A1 and a vertical-direction upper end 2B1 of the two corresponding joining sections 2 on the rear side are disposed apart from each other in the lateral direction, it is desirable that the buttocks expanding-contracting section 42 be positioned between a position p1 of the upper end 2A1 in the lateral direction and a position p2 of the upper end 2B1 in the lateral direction. That is, it is desirable that the first joining section 2A and the second joining section 2B on the rear side not overlap the buttocks expanding-contracting section 42 in the lateral direction.

A region (p1-p2) of the absorbent main body 10 that does not overlap the first joining section 2A and the second joining section 2B in the lateral direction is less likely to be subjected to a lateral-direction pulling force from each belt section 20 compared to a region of the absorbent main body 10 that overlaps the first joining section 2A and the second joining section 2B. Therefore, by disposing the buttocks expanding-contracting section 42 as described above, the buttocks expanding-contracting section 42 is less likely to expand in the lateral direction, such that it is possible to prevent the expansion of the buttocks expanding-contracting section 42 in the vertical direction from being hindered. Consequently, when pulling up the absorbent article 1, the buttocks expanding-contracting section 42 is capable of greatly expanding in the vertical direction, and the contraction amount of the buttocks expanding-contracting section 42 is correspondingly increased. Thus, the buttocks expanding-contracting section 42 is capable of causing the absorbent body 12 to firmly and closely fit the cleft between the buttocks of the wearer.

As shown in FIG. 4, it is desirable that an angle θ1 between a vertical center line CL1 that bisects the absorbent main body 10 in the lateral direction and each joining section 2 on the front side be greater than an angle θ2 between the vertical center line CL1 and each joining section 2 on the rear side. Specifically, the front angle θ1 may be in the range of 20 to 70 degrees, and may, more desirably, be in the range of 30 to 60 degrees. The rear angle θ2 may be in the range of 10 to 60 degrees, and may, more desirably, be in the range of 20 to 50 degrees.

As a result, on the front side where each joining section 2 is gently tilted, each belt section 20 tends to be tilted upward toward the outer side in the lateral direction; and, in contrast, on the rear side, each belt section 20 tends to be tilted upward toward the center in the lateral direction. Therefore, on the front side, it is possible to prevent the movement of the legs of the wearer who is, for example, walking from being hindered by the belt sections 20. On the other hand, on the rear side, the absorbent article 1 is pulled up to the vicinity of the sacral region that is positioned above the buttocks of the wearer. Consequently, looseness of the absorbent article 1 at the crotch of the wearer is suppressed and fittability of the absorbent article 1 is increased, such that it is possible to suppress leakage of excrement.

===Buttocks Expanding-Contracting Section 42 and Leg Gather Sections 30===

Figure 7:
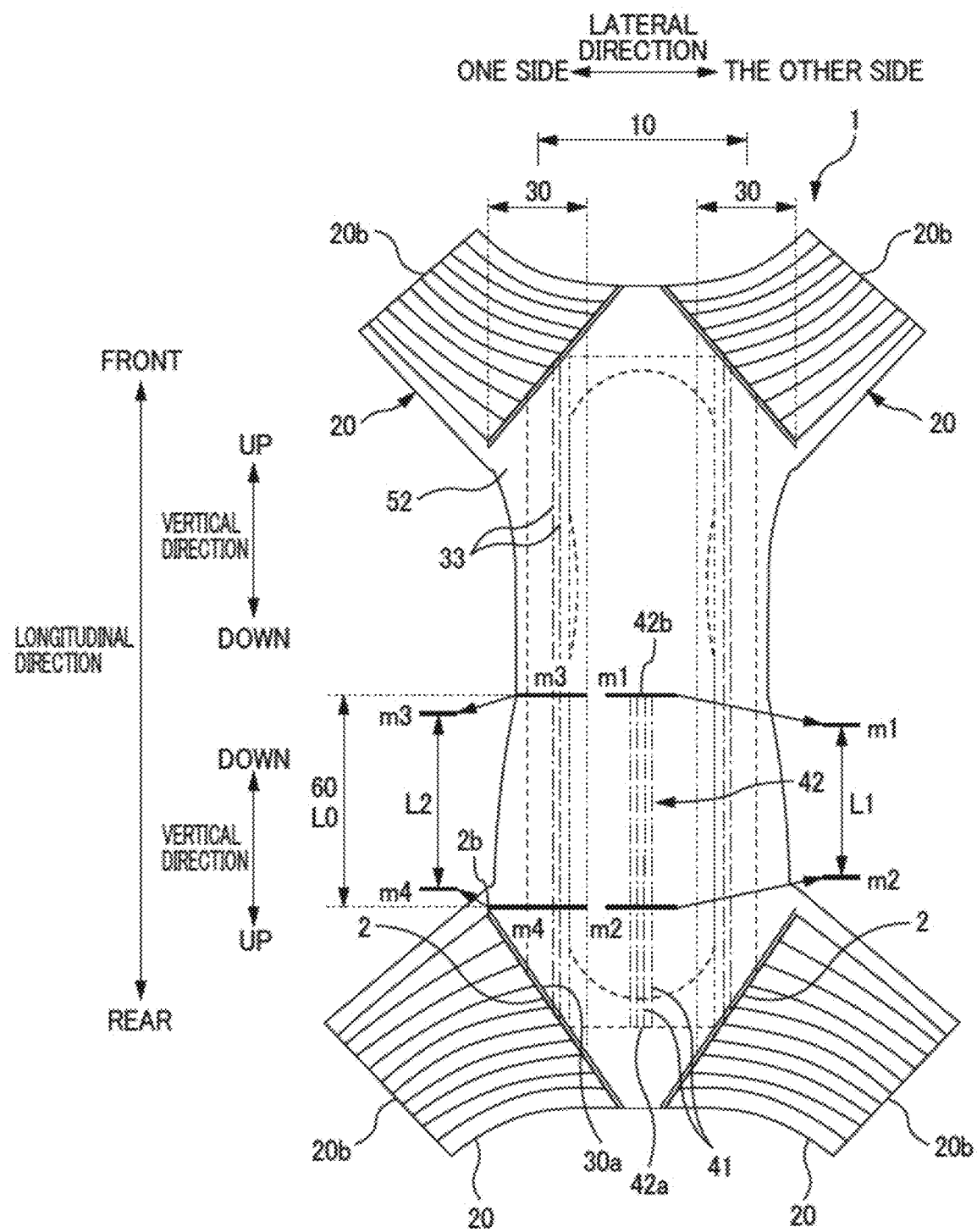
FIG. 7 illustrates the difference between the contraction amount of a buttocks expanding-contracting section 42 and the contraction amount of a leg gather section 30.

FIG. 7 illustrates the difference between the contraction amount of the buttocks expanding-contracting section 42 and the contraction amount of each leg gather section 30. The buttocks expanding-contracting section 42 and the leg gather sections 30 have an overlapping section 60 where they overlap each other in the vertical direction (longitudinal direction). When the absorbent article 1 has contracted from its expanded state to its natural state, it is desirable that the contraction amount in the vertical direction of the overlapping section 60 at the buttocks expanding-contracting section 42 be larger than the contraction amount in the vertical direction of the overlapping section 60 at each leg gather section 30.

The "overlapping section" of the buttocks expanding-contracting section 42 and the leg gather sections 30 may be the entire or part of the range where the buttocks expanding-contracting section 42 and each leg gather section 30 overlap each other in the vertical direction. In the absorbent article 1 of the present embodiment, the joining sections 2 are tilted, and upper ends 30a of the leg gather sections 30 in the vertical direction are also tilted. Therefore, in order to make it easy to compare the contraction amounts in the vertical direction described below, in the present embodiment, as shown in FIG. 7, part of the range where the buttocks expanding-contracting section 42 and each leg gather section 30 overlap each other in the vertical direction (that is, the range from the upper end 42a to the lower end 42b of the buttocks expanding-contracting section 42) is the overlapping section 60. Specifically, in the vertical direction, the range from a lower end 2b of each joining section 2 to the lower end 42b of the buttocks expanding-contracting section 42 is the overlapping section 60.

An example of the method of comparing the contraction amounts in the vertical direction is the following. First, in the absorbent article 1 in the pull-on state, an outer end 20b of each of the two belt sections 20 in the lateral direction is cut (at a location L1→L1 and a location L2→L2 in FIG. 5), and, as shown in FIG. 7, the absorbent main body 10 and each leg gather section 30 are fixed in an expanded state in the longitudinal direction.

The expanded state may be a maximally expanded state, or a state that is contracted compared to the maximally expanded state. Note that the maximally expanded state is a state in which the buttocks expanding-contracting section 42 and each leg gather section 30 are expanded in the longitudinal direction until wrinkles and the gathers can substantially no longer be seen in the buttocks expanding-contracting section 42 and each leg gather section 30. That is, the maximally expanded state is a state in which the sheets that make up the absorbent main body 10, such as the exterior sheet 14, and the sheets 51 that make up the leg gather sections 30 are expanded until each has a length that is equal to or approximately equal to the dimension thereof as an individual member.

Next, two longitudinal-direction ends of the overlapping section 60 at the buttocks expanding-contracting section 42 are provided with markers m1 and m2. Two longitudinal-direction ends of the overlapping section 60 at a leg gather section 30 are provided with markers m3 and m4. A longitudinal-direction length L0 of the overlapping section 60 in the expanded state is measured. That is, the longitudinal-direction length L0 from the markers m1 to m2 and the longitudinal-direction length L0 from the markers m3 and m4 are measured.

Next, the absorbent article 1 is brought out of the expanded state and is brought into the natural state (no-load state). Then, in the natural state, a longitudinal-direction length L1 of the overlapping section 60 at the buttocks expanding-contracting section 42 (length L1 from markers m1 to m2) and a longitudinal-direction length L2 of the overlapping section 60 at the leg gather section 30 (length L2 from markers m3 to m4) are measured. Then, when a value obtained by subtracting the length L1 from the length L0 (L0−L1) is larger than a value obtained by subtracting the length L2 from the length L0 (L0−L2), it can be confirmed that the contraction amount in the vertical direction of the overlapping section 60 at the buttocks expanding-contracting section 42 is larger than the contraction amount in the vertical direction of the overlapping section 60 at the leg gather section 30. Note that this comparison method is an example; however, a different method, such as a method of measuring the contraction amounts in the vertical direction in the pull-on state without unfolding the absorbent article 1 as in FIG. 7, may be used for comparing the contraction amounts.

If the contraction amount of each leg gather section 30 in the vertical direction is larger than the contraction amount of the buttocks expanding-contracting section 42 in the vertical direction, each leg gather section 30 hinders the contraction of the buttocks expanding-contracting section 42 in the vertical direction, and each leg gather section 30 closely fits the wearer more easily than the buttocks expanding-contracting section 42. This causes the absorbent article 1 to be deformed into the shape of a cup, as a result of which the buttocks expanding-contracting section 42 is less likely to closely fit the cleft between the buttocks of the wearer.

Therefore, the contraction amount of the buttocks expanding-contracting section 42 in the vertical direction may be made larger than the contraction amount of each leg gather section 30 in the vertical direction. That is, the expansion-contraction stress of the buttocks expanding-contracting section 42 may be made larger than the expansion-contraction stress of each leg gather section 30. Accordingly, the buttocks expanding-contracting section 42 is capable of causing the absorbent body 12 to firmly and closely fit the cleft between the buttocks of the wearer while the leg gather sections 30 closely fit around the respective legs of the wearer. Therefore, it is possible to suppress leakage of excrement from around the waist and rearward leakage of excrement.

Note that, in order to increase the contraction amount in the vertical direction, when, for example, thread-like elastic members are used, the diameter may be increased, the expansion ratio may be increased, or the number of thread-like elastic members may be increased; and when, for example, sheet-like elastic members are used, the expansion ratio may be increased or the width may be increased. The expansion ratio is the degree of expansion when the natural length of an elastic member is 1; for example, when the expansion ratio is 2.4, the elastic member is fixed to a sheet or the like with the elastic member expanded to a length that is 2.4 times the natural length from the natural length.

The buttocks expanding-contracting section 42 is provided with the plurality of thread-like elastic members (buttocks elastic members) 41 (here, four thread-like elastic members 41) disposed side by side in the lateral direction. On the other hand, each leg gather section 30 is provided with the sheet-like elastic member 52 along the corresponding leg opening LH and with the plurality of thread-like elastic members 33 (here, two thread-like elastic members 33) on the inner side of the sheet-like elastic member 52 in the lateral direction.

However, the configuration is not limited to the above, such that thread-like elastic members may be arranged around the leg openings LH of the leg gather sections 30. However, in this case, in order to suppress leakage of excrement, the expansion-contraction stress of each thread-like elastic member needs to be increased, thereby causing the thread-like elastic members to partly closely fit around the legs of the wearer and, thus, to place a burden on the skin. Therefore, it is desirable that the sheet-like elastic members 52 be arranged around the leg openings LH of the leg gather sections 30. This makes it possible to closely fit the leg gather sections 30 around the legs of the wearer at surfaces and to reduce the burden on the skin while properly suppressing leakage of excrement from around the legs.

When thread-like elastic members are arranged at the buttocks expanding-contracting section 42, the contraction amount in the vertical direction is easily increased and the buttocks expanding-contracting section 42 is capable of causing the absorbent body 12 to firmly and closely fit the cleft between the buttocks of the wearer compared to when sheet-like elastic members are arranged at the buttocks expanding-contracting section 42. Since the buttocks expanding-contracting section 42 is superimposed upon the absorbent body 12 that is thick, even if the thread-like elastic members 41 are arranged at the buttocks expanding-contracting section 42, they are less likely to place a burden on the skin.

===Buttocks Expanding-Contracting Section 42 and Waist Section 70===

As shown in FIG. 5, the absorbent article 1 includes a waist section 61 that includes the pair of belt sections 20, a front upper portion and a rear upper portion of the absorbent main body 10 in the vertical direction, and the vertical-direction upper portions of the two leg gather sections 30. The waist section 61 is expandable and contractable in the lateral direction. In the present embodiment, in the absorbent article 1, a region on the upper side of a location L3→L3 in the vertical direction shown in FIG. 5 is the waist section 61.

Note that, in the present embodiment, the belt sections 20 and the leg gather sections 30 are formed from the sheet members 50 that are similar, and the joining sections 2 do not reach the respective leg openings LH. Therefore, the joining sections 2 and extension lines thereof are the boundaries between the belt sections 20 and the leg gather sections 30.

Here, an expansion-contraction stress of the waist section 61 in the lateral direction when a length in the lateral direction of the waist section 61 in a maximally expanded state in the lateral direction is reduced to 61% from the maximally expanded state is called "waist expansion-contraction stress A". An expansion-contraction stress of the buttocks expanding-contracting section 42 in the vertical direction when a length in the vertical direction of the buttocks expanding-contracting section 42 in a maximally expanded state in the vertical direction is reduced to 82% from the maximally expanded state is called "buttocks expansion-contraction stress B".

When the absorbent article 1 is worn, the waist section 61 that has been greatly opened fits around the waist of the wearer while the waist section 61 contracts. The circumference of the waist section 61 when the waist section 61 has been contracted to 61% from the maximally expanded state of the waist section 61 corresponds to the average circumference of the human waist assumed for a wearer of the absorbent article 1. Therefore, the waist expansion-contraction stress A when the waist section 61 has been contracted to 61% from the maximally expanded state corresponds to the expansion-contraction stress of the waist section 61 when the waist section 61 fits around the waist of the wearer from the state in which the waist section 61 has been opened to be worn, that is, when the waist section 61 is worn. Similarly, the buttocks expanding-contracting section 42 fits the buttocks of the wearer while contracting after the buttocks expanding-contracting section 42 has been expanded in the vertical direction when pulling up the absorbent article 1. The state in which the buttocks expanding-contracting section 42 has been contracted to 82% from its maximally expanded state corresponds to a state in which the absorbent body 12 fits the average human buttocks assumed for a wearer of the absorbent article 1. Therefore, the buttocks expanding-contracting stress B also corresponds to the expansion-contraction stress of the buttocks expanding-contracting section 42 that is worn.

If the buttocks expansion-contraction stress B is larger than the waist expansion-contraction stress A, the waist section 61 tends to slip down due to the contraction of the buttocks expanding-contracting section 42 in the vertical direction. Therefore, it is desirable that the waist expansion-contraction stress A be larger than the buttocks expansion-contraction stress B (A>B). This makes it possible to, while closely fitting the absorbent body 12 to the cleft between the buttocks of the wearer by using the buttocks expanding-contracting section 42, cause the waist section 61 to fit the wearer and suppress the displacement of the waist section 61 that is worn.

Note that the maximally expanded state of the waist section 61 is a state in which the waist section 61 is expanded in the lateral direction until wrinkles and the gathers can substantially no longer be seen in the waist section 61, and is a state in which, for example, the sheets 51 that make up the belt sections 20 are expanded until each has a length that is equal to or approximately equal to the dimension thereof as an individual member. Similarly, the maximally expanded state of the buttocks expanding-contracting section 42 is a state in which the buttocks expanding-contracting section 42 (the absorbent main body 10) is expanded in the vertical direction until wrinkles and the gathers can substantially no longer be seen in the buttocks expanding-contracting section 42, and is a state in which the exterior sheet 14 and the like that make up the absorbent main body 10 are expanded until each has a length that is equal to or approximately equal to the dimension thereof as an individual member.

<Method of Measuring Expansion-Contraction Stresses A and B>

Figure 9:
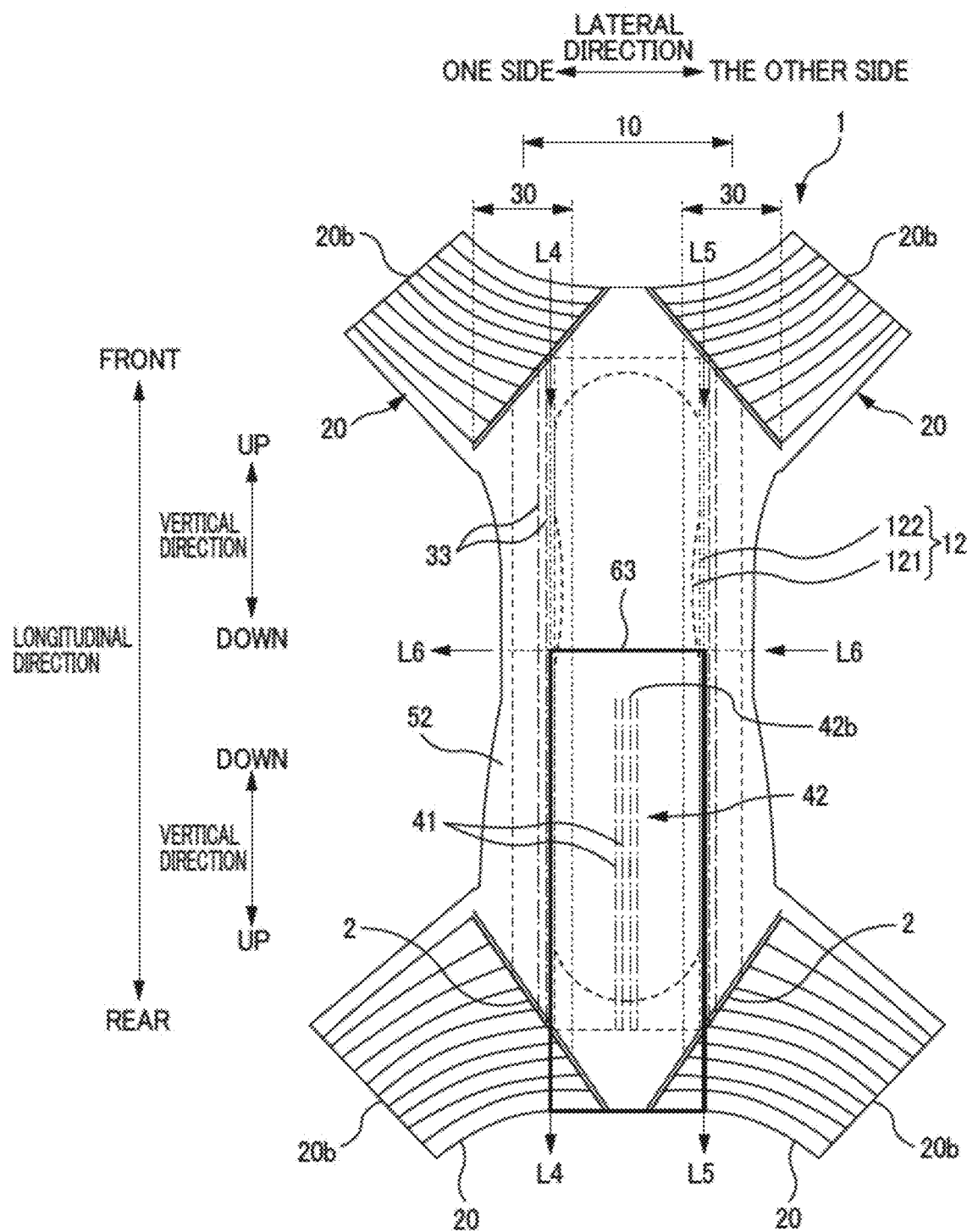
FIG. 9 is an explanatory view of a buttocks sample 63 used in measuring the buttocks expansion-contraction stress B.

FIG. 8 is a table of evaluated results obtained by measuring the expansion-contraction stress A and the expansion-contraction stress B of absorbent articles 1 of Examples 1 and 2 and Comparative Examples 1 and 2. FIG. 9 is an explanatory view of a buttocks sample 63 used in measuring the buttocks expansion-contraction stress B.

A waist sample 62 used in measuring the waist expansion-contraction stress A was acquired as follows. The absorbent article 1 in the pull-on state was cut at the location L3→L3 shown in FIG. 5, and a vertical-direction upper portion (waist section 61) above a cut line was acquired as the waist sample 62.

The buttocks sample 63 used in measuring the buttocks expansion-contraction stress B was acquired as follows. First, the absorbent article 1 in the pull-on state was cut at the location L1→L1 and the location L2→L2 shown in FIG. 5 (the outer ends 20b of the corresponding belt sections 20 in the lateral direction), and the absorbent article 1 was brought into the state shown in FIG. 9, that is, a state in which the absorbent main body 10 and the leg gather sections 30 were expanded in the longitudinal direction. Next, the absorbent article 1 shown in FIG. 9 was cut at a location L4→L4 and at a location L5→L5 in the longitudinal direction (both outer side portions located outward of the absorbent body 12 in the lateral direction) and was then cut at a location L6→L6 in the lateral direction, specifically, at a location situated forward of and 40 mm from the front side end 42b of the buttocks expanding-contracting section 42 in the longitudinal direction; and the buttocks sample 63 was acquired. Note that the thread-like elastic members 33 and the sheet-like elastic members 52 that the leg gather sections 30 include are not included in the buttocks sample 63.

The waist expansion-contraction stress A was measured as follows by using a tensile testing machine manufactured by Instron Japan Company Ltd. (INSTRON type: 5564). First, the waist sample 62 was caught by and fixed to a pair of jigs (not shown) arranged apart from each other in an up-down direction with an interval therebetween and having the form of thin rods. That is, the pair of jigs were passed through the inner side of the ring-shaped waist sample 62, and the up-down direction of the testing machine (the direction in which the pair of jigs were arranged side by side) and the lateral direction of the absorbent article 1 were aligned. The average waist circumference of a wearer of the absorbent article 1 (medium size) to be measured had a size of 732 mm, the circumference of the waist sample 62 in the maximally expanded state was 1200 mm, and a lateral direction length thereof was 600 mm (1200/2). Therefore, the interval of the pair of jigs in the up-down direction was set at 180 mm, which was less than 600 mm.

Next, the interval between the pair of jigs in the up-down direction was increased at a speed of 300 mm/min, and the waist sample 62 was expanded in the lateral direction of the absorbent article 1 until the waist sample 62 was brought into the maximally expanded state. That is, the interval between the pair of jigs in the up-down direction was further increased from the initial interval of 180 mm by 420 mm to increase the interval to 600 mm (100%). Then, the interval of the pair of jigs in the up-down direction was reduced at the same speed, and the waist sample 62 in the maximally expanded state was contracted in the lateral direction of the absorbent article 1. The expansion-contraction stress (N) when the length of the waist sample 62 in the lateral direction became 366 mm, which was 61% of the length in the maximally expanded state (600×0.61), that is, the expansion-contraction stress (N) in a state in which the waist sample 62 was expanded by 186 mm (=366−180) from its initial state was measured, and the measured value was defined as the waist expansion-contraction stress A.

Similarly, the buttocks expansion-contraction stress B was measured as follows by using the tensile testing machine manufactured by Instron Japan Company Ltd. (INSTRON type: 5564). First, both end portions of the buttocks sample 63 of the absorbent article 1 in the vertical direction (longitudinal direction) were held by a pair of chucks arranged apart from each other in the up-down direction with an interval therebetween. A vertical-direction length of the buttocks sample 63 in the maximally expanded state was 330 mm. Therefore, the interval between the pair of chucks was set at 170 mm (of which the holding width of the pair of chucks was 10 mm×2), which was less than 330 mm.

Next, the interval of the pair of chucks in the up-down direction was increased at a speed of 100 mm/min, and the buttocks sample 63 was expanded in the vertical direction of the absorbent article 1 until the buttocks sample 63 was brought into the maximally expanded state. That is, the interval between the pair of chucks in the up-down direction was further increased from the initial interval of 170 mm by 160 mm to increase the interval to 330 mm (100%). Then, the interval of the pair of chucks in the up-down direction was reduced at the same speed, and the buttocks sample 63 in the maximally expanded state was contracted in the vertical direction of the absorbent article 1. The expansion-contraction stress (N) when the length of the buttocks sample 63 in the vertical direction became 270 mm, which was 82% of the length in the maximally expanded state (330×0.82), that is, the expansion-contraction stress (N) in a state in which the buttocks sample 63 was expanded by 100 mm (=270−170) from its initial state was measured, and the measured value was defined as the buttocks expansion-contraction stress B.

As shown in FIG. 8, from each of the absorbent articles 1 of Examples 1 and 2 and Comparative Examples 1 and 2, the waist sample 62 and the buttocks sample 63 were acquired and the expansion-contraction stresses A and B were measured. Note that the basic configurations (configurations other than those of the elastic members) of the absorbent articles 1 of Examples 1 and 2 and Comparative Examples 1 and 2 are the same as each other, and correspond to the configuration of the absorbent article 1 described in the above-described embodiment.

Evaluation tests concerning "displacement around the waist" and "wedging into the buttocks" were performed on the absorbent articles 1 of Examples 1 and 2 and Comparative Examples 1 and 2.

Concerning displacement around the waist, displacement amounts of the waist sections 61 were evaluated when a wearer to be tested actually wore the absorbent articles 1, walked, squatted, sat, and the like. When there were displacements but the displacement amount was small, the result was "good", and when the displacement amount was in a tolerable range, the result was "tolerable".

Concerning wedging into the buttocks, the absorbent articles 1 were actually worn by a wearer to be tested, and how the wearer felt was evaluated. In the case where the wearer felt that the fittability of the absorbent body 12 with respect to the buttocks was good, the result was "good", whereas in the case where the wearer felt that the absorbent body 12 was slightly wedged into the buttocks but this was within a tolerable range, the result was "tolerable".

In Example 1 and Comparative Example 1, the configurations of the elastic members of the waist samples 62 differed from each other, but the configurations of the elastic members of the buttocks samples 63 are the same.

Specifically, at a region of an upper end portion folded back twice (see FIG. 2B) in each of the two belt sections 20 of the waist sample 62 of Example 1, six elastic strings having a diameter of 940 dtex and an expansion ratio of 3.2 were arranged at a pitch of 5 mm, and eleven elastic strings having a diameter of 940 dtex and an expansion ratio of 2.7 were arranged therebelow at a pitch of 5 mm.

At an upper end portion (not folded back) in each of the two belt sections 20 of the waist sample 62 of Comparative Example 1, six elastic strings having a diameter of 470 dtex and an expansion ratio of 3.2 were arranged at a pitch of 5 mm, and eleven elastic strings having a diameter of 620 dtex and an expansion ratio of 2.7 were arranged therebelow at a pitch of 5 mm.

In the buttocks sample 63 of Example 1 and the buttocks sample 63 of Comparative Example 1, four elastic strings having a diameter of 470 dtex and an expansion ratio of 2.2 were arranged at a pitch of 5 mm.

In contrast, in Example 2 and Comparative Example 2, although the configurations of the elastic members of the waist samples 62 were the same, the configurations of the elastic members of the buttocks samples 63 differed from each other.

Specifically, at a region of an upper end portion folded back twice in each of the two belt sections 20 of the waist sample 62 of each of Example 2 and Comparative Example 2, six elastic strings having a diameter of 1240 dtex and an expansion ratio of 3.2 were arranged at a pitch of 5 mm, and eleven elastic strings having a diameter of 1240 dtex and an expansion ratio of 2.7 were arranged therebelow at a pitch of 5 mm.

In the buttocks sample 63 of Example 2, four elastic strings having a diameter of 620 dtex and an expansion ratio of 2 were arranged at a pitch of 5 mm.

In the buttocks sample 63 of Comparative Example 2, four elastic strings having a diameter of 780 dtex and an expansion ratio of 2.2 were arranged at a pitch of 5 mm.

As a result of the measurements, as shown in FIG. 8, the waist expansion-contraction stress A of Example 1 was 5.56 (N), the waist expansion-contraction stress A of Comparative Example 1 was 2.62 (N), and the buttocks expansion-contraction stress B of Example 1 and the buttocks expansion-contraction stress B of Comparative Example 1 were 0.37 (N). In Example 1, the results concerning displacement around the waist and wedging into the buttocks were both "good". In Comparative Example 1, although the result concerning wedging into the buttocks was "good", the result concerning displacement around the waist was "tolerable".

That is, it was found that when the buttocks expansion-contraction stress B was set so as not to cause wedging into the buttocks, in the case where the waist expansion-contraction stress A was 15 times this buttocks expansion-contraction stress B, the result concerning displacement around the waist was "good", whereas in the case where the waist expansion-contraction stress A was 7.1 times this buttocks expansion-contraction stress B, the result concerning displacement around the waist was "tolerable".

On the other hand, the waist expansion-contraction stress A of Example 2 and the waist expansion-contraction stress A of Comparative Example 2 were 6.56 (N), the buttocks expansion-contraction stress B of Example 2 was 0.54 (N), and the buttocks expansion-contraction stress B of Comparative Example 2 was 0.98 (N). In Example 2, the result concerning displacement around the waist and the result concerning wedging into the buttocks were both "good". In Comparative Example 2, although the result concerning displacement around the waist was "good", the result concerning wedging into the buttocks was "tolerable".

That is, it was found that, when the waist expansion-contraction stress A was set so as not to cause displacement around the waist, in the case where the buttocks expansion-contraction stress B was 1/12.1 times this waist expansion-contraction stress A, the result concerning wedging into the buttocks was "good", whereas in the case where the buttocks expansion-contraction stress B was 1/6.7 times this waist expansion-contraction stress A, the result concerning wedging into the buttocks was "tolerable".

Even in Comparative Examples 1 and 2, compared to when the buttocks expansion-contraction stress B is larger than the waist expansion-contraction stress A, it is possible to suppress displacement of the waist section 61 that is worn while causing the absorbent body 12 to closely fit the cleft between the buttocks of the wearer by using the buttocks expansion-contracting section 42. However, the results of FIG. 8 show that it is more desirable that the waist expansion-contraction stress A be 7.1 times greater than the buttocks expansion-contraction stress B (A/B>7.1). In this case, it is possible to suppress displacement of the waist section 61 that is worn while making the absorbent article more comfortable to wear by reducing discomfort that the wearer feels when wearing the absorbent article due to the absorbent body 12 being excessively wedged into the buttocks.

Although the embodiment of the present invention has been described, the above-described embodiment is an embodiment for facilitating the understanding of the present invention and is not to be construed as limiting the present invention. The present invention can be modified and improved without departing from the spirit of the present invention and it is needless to say that the present invention includes equivalents thereof.

The invention claimed is:

1. A pull-on absorbent article having a vertical direction, a lateral direction, and a front-rear direction and including a waist opening and a pair of leg openings, the pull-on absorbent article comprising:
   a waist section;
   an absorbent main body that includes an absorbent body and that is provided in the vertical direction; and
   a pair of belt sections that are each disposed on a corresponding side of the absorbent main body in the lateral direction and that expand and contract in the lateral direction,
   wherein
   pairs of joining sections that join at least the absorbent main body and the pair of belt sections to each other are provided, one pair being disposed on a front side and the other pair being disposed on a rear side in the front-rear direction, at least a portion between the pair of joining sections on the rear side does not expand and contract in the lateral direction, an expanding-contracting section that expands and contracts in the vertical direction is provided closer than the absorbent body to a non-skin side of a wearer, in at least the rear side, the expanding-contracting section is provided at a central portion of the absorbent main body in the lateral direction, the waist section includes at least the pair of belt sections and an upper portion on the front side and an upper portion on the rear side of the absorbent main body in the vertical direction, and an expansion-contraction stress of the waist section in the lateral direction when a length in the lateral direction of the waist section in a maximally expanded state in the lateral direction is reduced to 61% from the maximally expanded state is larger than an expansion-contraction stress of the expanding-contracting section in the vertical direction when a length in the vertical direction of the expanding-contracting section in a maximally expanded state in the vertical direction is reduced to 82% from the maximally expanded state.

2. The pull-on absorbent article according to claim 1, wherein, in the vertical direction, an upper end of the expanding-contracting section is positioned so as to match a position of an upper end of the absorbent body or is positioned on a lower side of the upper end of the absorbent body.

3. The pull-on absorbent article according claim 1, wherein, in the vertical direction, a lower end of the expanding-contracting section is positioned so as to match a position of a lower end of the pull-on absorbent article or is positioned on the rear side and an upper side of the lower end of the pull-on absorbent article.

4. A pull-on absorbent article having a vertical direction, a lateral direction, and a front-rear direction and including a waist opening and a pair of leg openings, the pull-on absorbent article comprising:

an absorbent main body that includes an absorbent body and that is provided in the vertical direction; and a pair of belt sections that are each disposed on a corresponding side of the absorbent main body in the lateral direction and that expand and contract in the lateral direction, wherein pairs of joining sections that join at least the absorbent main body and the pair of belt sections to each other are provided, one pair being disposed on a front side and the other pair being disposed on a rear side in the front-rear direction, at least a portion between the pair of joining sections on the rear side does not expand and contract in the lateral direction, an expanding-contracting section that expands and contracts in the vertical direction is provided closer than the absorbent body to a non-skin side of a wearer, in at least the rear side, the expanding-contracting section is provided at a central portion of the absorbent main body in the lateral direction, the pull-on absorbent article further comprises a pair of leg gather sections that are each disposed on a corresponding side of the absorbent main body in the lateral direction and that expand and contract in the vertical direction, the expanding-contracting section and the leg gather sections have an overlapping section where the expanding-contracting section and each leg gather section overlap each other in the vertical direction, and when the absorbent article has contracted from an expanded state to a natural state, a contraction amount in the vertical direction of the overlapping section at the expanding-contracting section is larger than a contraction amount in the vertical direction of the overlapping section at each leg gather section.

5. The pull-on absorbent article according to claim 4, wherein the expanding-contracting section is provided with a plurality of thread-like elastic members that are arranged side by side in the lateral direction, and wherein each leg gather section is provided with a sheet-like elastic member at least along the leg opening corresponding thereto.

6. A pull-on absorbent article having a vertical direction, a lateral direction, and a front-rear direction and including a waist opening and a pair of leg openings, the pull-on absorbent article comprising:

an absorbent main body that includes an absorbent body and that is provided in the vertical direction; and a pair of belt sections that are each disposed on a corresponding side of the absorbent main body in the lateral direction and that expand and contract in the lateral direction, wherein pairs of joining sections that join at least the absorbent main body and the pair of belt sections to each other are provided, one pair being disposed on a front side and the other pair being disposed on a rear side in the front-rear direction, at least a portion between the pair of joining sections on the rear side does not expand and contract in the lateral direction, an expanding-contracting section that expands and contracts in the vertical direction is provided closer than the absorbent body to a non-skin side of a wearer, in at least the rear side, the expanding-contracting section is provided at a central portion of the absorbent main body in the lateral direction, in the vertical direction, each joining section is tilted outward in the lateral direction toward the leg opening corresponding thereto from a side of the waist opening, and a perpendicular line that is perpendicular to the joining sections on the rear side crosses the expanding-contracting section.

7. The pull-on absorbent article according to claim 6, wherein the perpendicular line is a perpendicular bisector of the joining sections on the rear side.

8. The pull-on absorbent article according to claim 1, wherein, in the vertical direction, each joining section is tilted outward in the lateral direction toward the leg opening corresponding thereto from a side of the waist opening, and wherein upper ends of the pair of joining sections on the rear side in the vertical direction are disposed apart from each other in the lateral direction, and the expanding-contracting section is positioned between positions of the upper ends in the lateral direction.

* * * * *